US00PP13348P2

(12) United States Plant Patent
Heims

(10) Patent No.: US PP13,348 P2
(45) Date of Patent: Dec. 10, 2002

(54) HEUCHERA PLANT NAMED 'AMBER WAVES'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/718,626

(22) Filed: Nov. 21, 2000

(51) Int. Cl.[7] ..... A01H 5/00
(52) U.S. Cl. ..... Plt./263
(58) Field of Search ..... Plt./263

*Primary Examiner*—Gruce R. Campell
*Assistant Examiner*—Kent L. Bell
(74) *Attorney, Agent, or Firm*—Klarquist Sparkman, LLP

(57) ABSTRACT

A new and distinct Heuchera plant charaterized by unique amber-colored, ruffled leaves.

2 Drawing Sheets

The present invention relates to a new and distinct variety of Heuchera hybrid, of the family Saxifragaceae, which originated as a sport mutation of an unpatented Heuchera plant named 'Whirlwind'. As Heuchera 'Whirlwind' is of hybrid origin (unpatented), no species specification is given for the instant plant.

The instant plant developed as the result of the applicant's idea to isolate and tissue culture the petiole off of a gold leaf found sporting from a Heuchera 'Whirlwind'. The new variety has been reproduced only by asexual propagation (tissue culture and division). Each of the progeny exhibits identical characteristics to the original plant.

This plant is characterized by the following:

1. Unique, amber-colored foliage.
2. Ruffled foliage.

Asexual propagation by division and tissue culture, using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
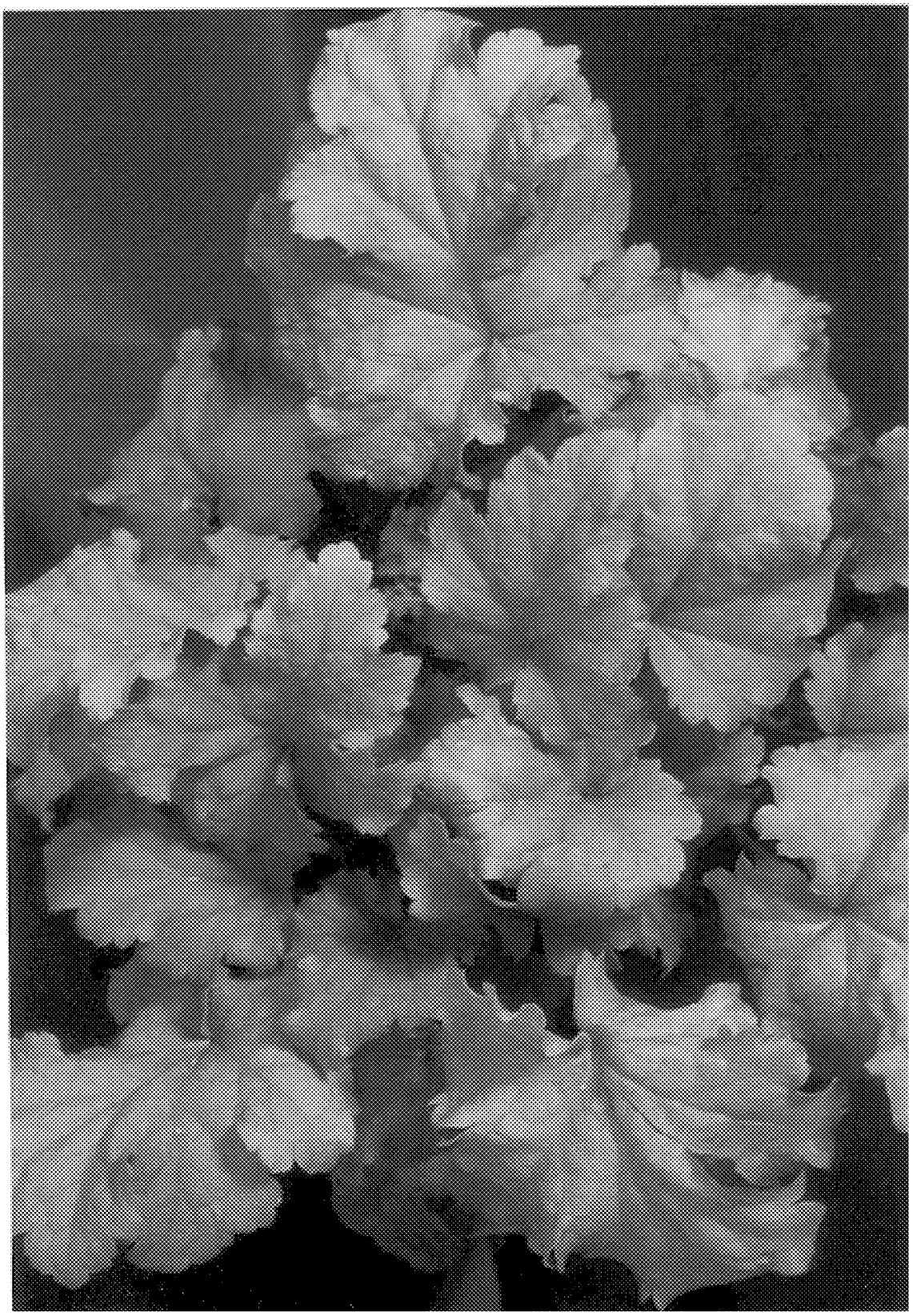
FIG. 1 shows the foliage of a two-year-old plant of Heuchera 'Amber Waves' in summer.
Figure 2:
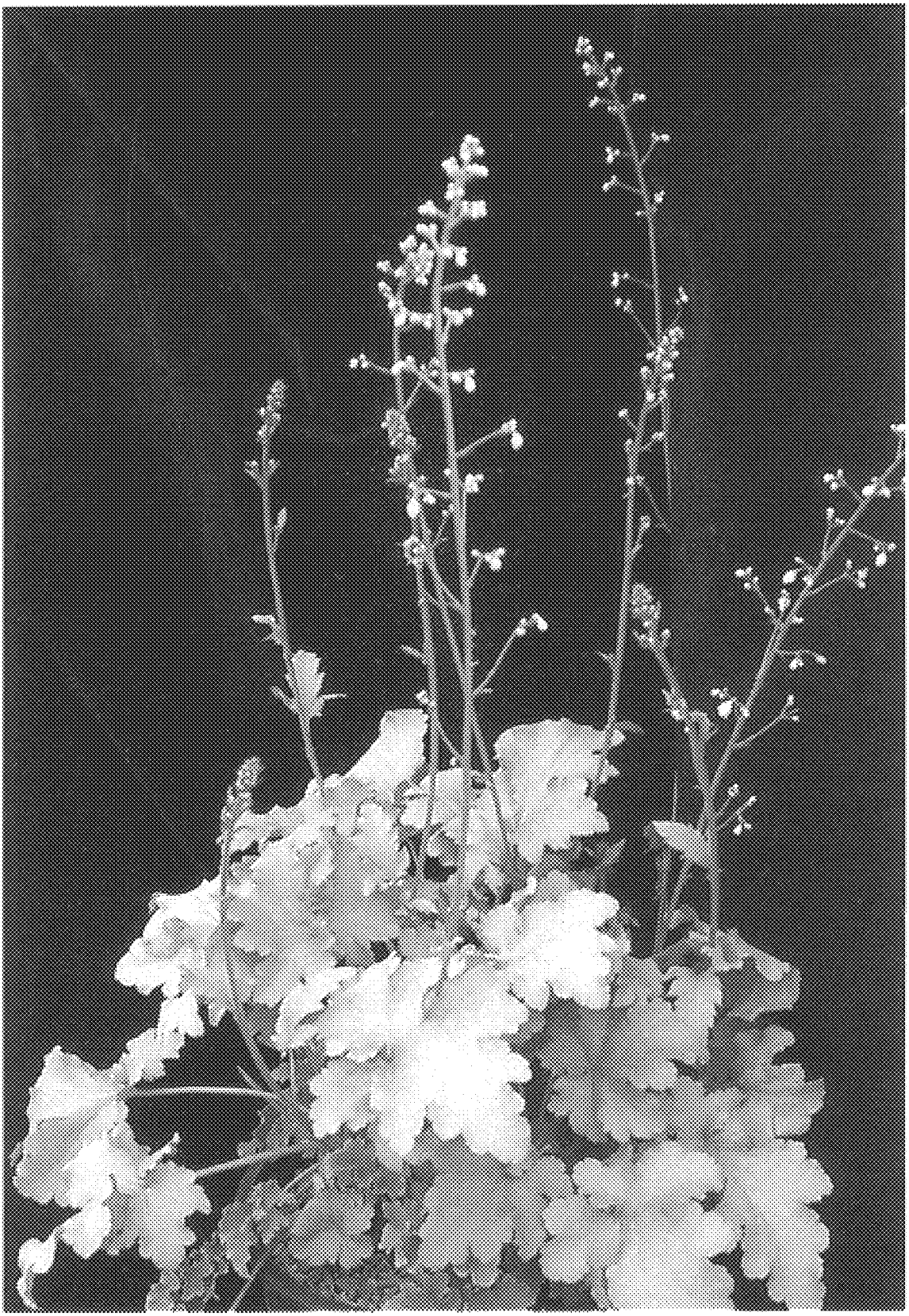
FIG. 2 shows a whole plant of the new cultivar growing in a one gallon pot in the spring.

The following is a detailed description of the new Heuchera based on observations of one-and-a-half year old specimens grown in the ground in Canby, Oreg. The color descriptions are all based on The Royal Horticultural Society Colour Chart.

Foliage:
- *Type*.—Simple. Evergreen.
- *Shape*.—Ovate to cordate.
- *Length*.—5.5–8 cm.
- *Width*.—6.5–10 cm.
- *Petiole length*.—8–10 cm.
- *Margins*.—Dentate-ciliate-sinuate.

- *Apex*.—Broadly acute to rounded.
- *Base*.—Deeply cordate and overlapping.
- *Leaf texture*.—Puberulent.
- *Petiole texture*.—Sparsely pubescent.
- *Leaf arrangement*.—Rosette.
- *Venation*.—Reticulate.

Size of plant without flowers: (1.5-year-old plants grown in the ground in Canby, Oreg.:
- *Height*.—To 25 cm.
- *Width*.—To 40 cm.

Flower:
- *Type*.—Perfect, zygomorphic.
- *Shape*.—Campanulate.
- *Size*.—0.7 cm deep and 0.4 cm wide.
- *Petal count*.—5.
- *Petal shape*.—Elliptic with a clawed base, reflexed.
- *Petal size*.—2 mm.
- *Calyx*.—Divided to ½ the way to the base, with glandular hairs, urceolate.
- *Sepal number*.—5 lobes.
- *Sepal size*.—0.6 cm deep and 0.4 cm wide.
- *Stamen number*.—5.
- *Pistil number*.—1, with 2 styles, and a one-celled ovary, typical of the genus.
- *Inflorescence type*.—Panicle.
- *Flower number per inflorescence*.—20–50.
- *Peduncle height*.—30 cm.
- *Peduncle width*.—2 mm tapering to 1 mm.
- *Peduncle texture*.—Puberulent.
- *Pedicel*.—Grows from 0.5 to 3 cm.
- *Bloom period*.—April to June.
- *Fragrance*.—None.
- *Lastingness*.—Individual bloom lasts up to 3 days but a panicle may last up tp 14 days.

Fruit:
- *Type*.—Two-beaked ovoid capsule.
- *Fertility*.—Low.

Seed:
- *Shape*.—Linear.
- *Size*.—2 mm. long.

Habit: Clumping.

Disease: May be susceptible to rust when grown under sub-optimal conditions. Have not observed other diseases on plants grown commercially in Canby, Oreg.

Hardiness: Cold hardy to USDA zone 4.

Color Characteristics

Foliage: Plants become greener under periods of low light as observed in fall and winter. Optimal amber coloration is observed from late spring through summer.

Spring/summer:

*Upper surface*.—Varies from RHS 153C and 152D Yellow-Green Group.

*Upper surface, emerging foliage*.—Between RHS 163A and B, Greyed-Orange Group.

*Lower surface*.—RHS 72A Red-Purple Group.

*Lower surface, emerging foliage*.—Between RHS 59B and 60B, Red-Purple Group.

Fall:

*Upper surface*.—Varies from RHS 146B and C, Yellow-Green Group to RHS 166B and C, Greyed-Orange Group.

Petiole:

*Spring and summer*.—RHS 186B, Greyed-Purple Group.

*Fall and winter*.—RHS 177B, Greyed-Orange Group.

Flower:

*Closed buds*.—Between RHS 37B and C, Red Group.

*Open buds* (*petals and sepals combined*).—Varies from RHS 36B Red Group to RHS 157B–D Green-White Group.

*Petals* (*both surfaces*).—RHS 36D Red Group.

*Sepals* (*both surfaces*).—RHS 36C, Red Group.

*Anther*.—Between RHS 25A and B, Orange Group.

*Pistil*.—RHS 185B Yellow White Group.

*Pollen*.—RHS 28A, Orange Group.

Peduncle and pedicel:

*Spring*.—RHS 185B Greyed-Purple Group.

*Summer*.—RHS 177B Greyed-Orange Group.

Fruit: Tan. RHS 160C Greyed-Yellow to 199C Grey-Brown.

Seed:

*Color*.—Black. RHS 202A.

DESCRIPTION OF PARENT PLANT

Heuchera 'Whirlwind' resulted from a cross, made by the applicant, between a sharply ruffled unpatented, and unnamed *Heuchera micrantha* seedling and an unpatented Heuchera named 'Palace Passion'. Heuchera 'Whirlwind' has fluted and crested dark bronze foliage and pink to white flowers. The instant plant differs from its parent in foliar coloration.

I claim:

1. A new and distinct Heuchera plant substantially as shown and described, characterized by unique amber-colored, ruffled leaves.

* * * * *